(12) United States Patent
Sung et al.

(10) Patent No.: US 12,138,084 B2
(45) Date of Patent: Nov. 12, 2024

(54) MOBILE BATTERY POWERED MEDICAL CART

(71) Applicant: Green Cubes Technology, LLC, Kokomo, IN (US)

(72) Inventors: Goo Sung, Everett, WA (US); Mohammed Alobaidi, Kokomo, IN (US); Calvin Ting, Kokomo, IN (US)

(73) Assignee: Green Cubes Technology, LLC, Kokomo, IN (US)

( * ) Notice: Subject to any disclaimer, the term of this patent is extended or adjusted under 35 U.S.C. 154(b) by 914 days.

(21) Appl. No.: 17/259,014

(22) PCT Filed: Jul. 9, 2019

(86) PCT No.: PCT/US2019/041084
§ 371 (c)(1),
(2) Date: Jan. 8, 2021

(87) PCT Pub. No.: WO2020/014284
PCT Pub. Date: Jan. 16, 2020

(65) Prior Publication Data
US 2021/0267707 A1 Sep. 2, 2021

Related U.S. Application Data

(60) Provisional application No. 62/695,501, filed on Jul. 9, 2018.

(51) Int. Cl.
*A61B 50/13* (2016.01)
*G06F 3/01* (2006.01)
(Continued)

(52) U.S. Cl.
CPC .............. *A61B 50/13* (2016.02); *G06F 3/016* (2013.01); *G06N 5/02* (2013.01); *G16H 40/67* (2018.01);
(Continued)

(58) Field of Classification Search
CPC ............ A61B 50/13; A61B 2560/0214; A61B 2560/0487; A61B 2560/0493; G06F 3/016; G06N 5/02; G16H 40/67
See application file for complete search history.

(56) References Cited

U.S. PATENT DOCUMENTS 6,099,093 A * 8/2000 Spence ................... A47B 21/03
108/50.01
9,367,061 B2 * 6/2016 Miller .............. G10K 11/17873
(Continued)

FOREIGN PATENT DOCUMENTS

CA         3106166 A1 * 1/2020 ............. A61B 50/13
WO  WO-2020014284 A1 * 1/2020 ............. A61B 50/13

OTHER PUBLICATIONS

International Searching Authority, International Search Report, PCT/US2019/041084, dated Nov. 15, 2019.
(Continued)

*Primary Examiner* — Jacob B Meyer
(74) *Attorney, Agent, or Firm* — Reichel Stohry Dean LLP; Mark C. Reichel; Natalie J. Dean (57) ABSTRACT

Disclosed herein are mobile battery powered medical carts, methods of operating these carts to increase efficiency of healthcare operations, and methods of accurately calculating remaining battery runtime for these carts. A mobile battery powered medical cart may comprise a wheeled base portion having a sliding battery power bay, an upper workstation area having a monitor, a computer, and a printer, and at least one adjustable height column coupling the wheeled base portion to the upper workstation area. The carts may include a glass overlay display positioned on a top surface of the upper workstation area and having anti-bacterial and chemical resistant properties. The glass overlay display may be configured to provide medical employees with haptic feed- (Continued)

back on remaining battery runtime, calculated via a custom algorithm for increased accuracy.

20 Claims, 8 Drawing Sheets

(51) Int. Cl.
    *G06N 5/02*     (2023.01)
    *G16H 40/67*     (2018.01)
    *H02J 7/00*     (2006.01)

(52) U.S. Cl.
    CPC ............... *A61B 2560/0214* (2013.01); *A61B 2560/0487* (2013.01); *A61B 2560/0493* (2013.01); *H02J 7/0048* (2020.01)

(56) References Cited

U.S. PATENT DOCUMENTS

| | | | | |
|---|---|---|---|---|
| 9,475,514 | B2 * | 10/2016 | Hardy | A61G 12/001 |
| 10,188,477 | B1 * | 1/2019 | Norman | A61B 50/33 |
| 10,453,572 | B1 * | 10/2019 | Brooks | G16H 40/40 |
| 11,223,227 | B1 * | 1/2022 | Phillips | G06F 1/263 |
| 11,866,081 | B2 * | 1/2024 | Alobaidi | B62B 3/005 |
| 2003/0046554 | A1 * | 3/2003 | Leydier | G07C 9/257 |
| | | | | 713/186 |
| 2003/0232238 | A1 * | 12/2003 | Fleming | H01M 10/121 |
| | | | | 429/211 |
| 2004/0102690 | A1 * | 5/2004 | Bartels | A61G 7/1046 |
| | | | | 600/407 |
| 2010/0001870 | A1 * | 1/2010 | Hong | H01M 10/48 |
| | | | | 702/58 |
| 2012/0086163 | A1 * | 4/2012 | Wardak | B65H 3/48 |
| | | | | 271/104 |
| 2013/0076137 | A1 * | 3/2013 | Murtha | H01M 10/482 |
| | | | | 307/48 |
| 2014/0276180 | A1 * | 9/2014 | Dextradeur | A61B 5/0031 |
| | | | | 600/544 |
| 2015/0223890 | A1 * | 8/2015 | Miller | A61B 50/10 |
| | | | | 726/17 |
| 2015/0223891 | A1 * | 8/2015 | Miller | A61B 50/15 |
| | | | | 726/19 |
| 2015/0223892 | A1 * | 8/2015 | Miller | A61B 50/18 |
| | | | | 345/174 |
| 2015/0227127 | A1 * | 8/2015 | Miller | G16H 20/13 |
| | | | | 700/244 |
| 2016/0042139 | A1 * | 2/2016 | Uttley | B62B 1/26 |
| | | | | 280/652 |
| 2016/0367329 | A1 * | 12/2016 | Dekel | A61B 50/20 |
| 2017/0005512 | A1 * | 1/2017 | Boyd | H01M 50/247 |
| 2017/0030882 | A1 * | 2/2017 | Skoda | A61M 15/0003 |
| 2017/0251990 | A1 * | 9/2017 | Kheradpir | A61B 50/13 |
| 2021/0267707 | A1 * | 9/2021 | Sung | G16H 40/67 |
| 2021/0318724 | A1 * | 10/2021 | Sung | B62B 3/02 |
| 2022/0071827 | A1 * | 3/2022 | Phillips | H02J 9/06 |

OTHER PUBLICATIONS

International Searching Authority, Written Opinion of the International Searching Authority, PCT/US2019/041084, dated Nov. 15, 2019.

Canadian Intellectual Property Office, Examiners Requisition, Canadian Application No. 3,106,166, Dated Jan. 22, 2024.

* cited by examiner

MOBILE BATTERY POWERED MEDICAL CART

PRIORITY

The present application is related to, and claims the priority benefit of, U.S. Provisional Patent Application Ser. No. 62/695,501, filed on Jul. 9, 2018, the contents of which are hereby incorporated into the present disclosure in their entirety.

BACKGROUND

Hospitals can become extremely crowded and busy, especially in emergency situations. When a hospital is experiencing very high patient volume, such as during an emergency situation, there may not be enough desk computers available which can cause unnecessary delay. Thus, it may be desirable for hospitals to have extra mobile battery powered medical carts on location, so that they may be utilized to process more patients (and to do so more efficiently) during high patient volume situations. Additionally, hospital and medical office professionals often want to have the computer in the room during patient treatment, and so it may be desirable to move the computer directly to the patient's room (or other location) for more efficient medical treatment. Having a mobile battery powered medical cart that contains the computer, extra batteries, medical equipment, supplies, etc., and which can easily be moved to any location or room within a medical office or hospital, would certainly be desirable.

Due to the high risk of infection in hospitals and medical office settings, it would also be desirable to have a mobile battery powered medical cart with a chemical resistant or anti-bacterial glass overlay for easy cleaning. Furthermore, currently available mobile battery powered medical carts may often miscalculate and incorrectly display remaining battery life expectancy. Thus, having a cart with easily replaceable batteries and more accurate calculation and display of remaining battery life would also be desirable for medical staff. It would further be desirable to have a mobile battery powered medical cart that integrates a voice activated smart hub, an internal RFID system, GPS and/or GPS locator, WiFi, and/or Bluetooth Low Energy (BLE) for ease of cart location and integration into existing hospital services and operations.

BRIEF SUMMARY

In one embodiment, a mobile battery powered medical cart, comprises: a wheeled base portion having a battery power bay for service and battery replacement therein; an upper workstation area having a monitor and a glass overlay display, wherein the glass overlay display is positioned on a top surface of the upper workstation area and has anti-bacterial and chemical resistant properties and comprises haptic feedback controls; at least one adjustable height column operably coupling the wheeled base portion and the upper workstation area and electronically coupling the battery in the wheeled base portion with the monitor and haptic feedback controls in the upper workstation area.

In another embodiment, a mobile battery powered medical cart, comprises: a wheeled base portion having a battery power bay for receiving at least one swappable battery therein; an upper workstation area having electronic components operably coupled to, and powered by, the battery in the power bay; a glass overlay display positioned on a top surface of the upper workstation area and having anti-bacterial and chemical resistant properties, and providing a display for remaining battery runtime calculated via a custom runtime algorithm; and a technology bay to house integrated RFID, Wi-Fi, BLE, and/or GPS systems.

In yet another embodiment, a method of calculating remaining battery runtime in a mobile battery powered medical cart, comprises: determining a set power consumption rate (Pset), wherein Pset is the average power consumption of all electronic devices and accessories connected to the battery powered medical cart, and wherein Pset is determined during production or manufacture of the battery powered mobile medical cart; and applying a custom runtime algorithm, wherein remaining battery runtime is calculated by taking remaining battery capacity (in Watt/hour) and dividing it by the set power consumption rate (Pset).

The present disclosure includes disclosure of mobile battery powered medical carts, comprising a wheeled base portion having a battery power bay for service and battery replacement therein; an upper workstation area having a monitor and a glass overlay display, wherein the glass overlay display is positioned on a top surface of the upper workstation area and has anti-bacterial and chemical resistant properties and comprises haptic feedback controls; at least one adjustable height column operably coupling the wheeled base portion and the upper workstation area and electronically coupling the battery in the wheeled base portion with the monitor and haptic feedback controls in the upper workstation area. In at least one embodiment, the haptic feedback controls are used to control passcode input, adjustment of the adjustable height column, workspace illumination controls, and display of remaining battery runtime via a custom runtime algorithm. In at least one embodiment, remaining battery runtime is calculated by taking remaining battery capacity (in Watt/hour) and dividing it by the set power consumption rate (Pset), wherein Pset is the average power consumption of all electronic devices and accessories connected to the battery powered mobile medical cart, and wherein Pset is determined during production or manufacture of the battery powered mobile medical cart. In at least one embodiment, the medical cart further comprises a voice activated smart hub or artificial intelligence hub. In at least one embodiment, the medical cart further comprises a technology bay in the upper workstation area to house a computer, an RFID reader, Wi-Fi, BLE, and/or GPS systems. In at least one embodiment, the medical cart further comprises an RFID device that is integrated with the glass overlay display. In at least one embodiment, the at least one adjustable height column comprises low friction compressible material for smooth and stable vertical motion during adjustment. In at least one embodiment, the medical cart further comprises a slide out keyboard tray comprising precision linear ball-bearing guiderails positioned on the upper workstation area. In at least one embodiment, the battery power bay comprises modular compartments for receiving multiple batteries therein, wherein more than one battery may be used to adjust runtime of the cart. In at least one embodiment, the medical cart further comprises battery separating tabs disposed between the battery compartments of the battery power bay to reduce heat and/or improve individual battery performance. In at least one embodiment, the battery power bay is operable via sliding. In at least one embodiment, the monitor further comprises a laptop computer or tablet. In at least one embodiment, the medical cart further comprises a computer. In at least one embodiment, the computer is positioned below the upper workstation area. In at least one embodiment, the medical cart further comprises a printer. In at least one embodiment, the medical cart further comprises storage below the upper workstation area, for storage of medical supplies or medical equipment. In at least one embodiment, the medical cart further comprises a bracket on the at least one adjustable height column for storing at least one spare battery. In at least one embodiment, the at least one adjustable height column comprises two adjustable height columns spaced apart to provide additional space therebetween.

The present disclosure includes disclosure of mobile battery powered medical carts, comprising a wheeled base portion having a battery power bay for receiving at least one swappable battery therein; an upper workstation area having electronic components operably coupled to, and powered by, the battery in the power bay; a glass overlay display positioned on a top surface of the upper workstation area and having anti-bacterial and chemical resistant properties, and providing a display for remaining battery runtime calculated via a custom runtime algorithm; and a technology bay to house integrated RFID, Wi-Fi, BLE, and/or GPS systems. In at least one embodiment, the medical cart further comprises a voice activated smart hub or artificial intelligence hub. In at least one embodiment, the medical cart further comprises at least one adjustable height column comprising a low friction compressible material for smooth and stable vertical motion during adjustment. In at least one embodiment, the medical cart further comprises a barcode reader/scanner positioned on the upper workstation area. In at least one embodiment, the medical cart further comprises a slide out keyboard tray using precision linear ball-bearing guiderails positioned on the upper workstation area. In at least one embodiment, the battery power bay comprises modular compartments for receiving multiple batteries therein, wherein more than one battery may be used to adjust runtime of the cart. In at least one embodiment, the medical cart further comprises battery separating tabs disposed between the battery compartments of the battery power bay to reduce heat and/or improve individual battery performance. In at least one embodiment, the battery power bay operates by sliding. In at least one embodiment, the glass overlay display further comprises haptic feedback controls for passcode input, adjustment of at least one adjustable height column, workspace illumination controls, and display of remaining battery life via custom runtime algorithm. In at least one embodiment, remaining battery runtime is calculated using an algorithm, taking remaining battery capacity (in Watt/hour) and dividing it by the set power consumption rate (Pset), wherein Pset is the average power consumption of all electronic devices and accessories connected to the mobile battery powered medical cart, and wherein Pset is determined during production or manufacture of the mobile battery powered medical cart. In at least one embodiment, the medical cart further comprises a monitor. In at least one embodiment, the medical cart further comprises a computer. In at least one embodiment, the computer is positioned below the upper workstation area. In at least one embodiment, the medical cart further comprises a printer. In at least one embodiment, the medical cart further comprises storage below the upper workstation area, for storage of medical supplies or medical equipment. In at least one embodiment, the medical cart further comprises a bracket on the at least one adjustable height column for storing at least one spare battery. In at least one embodiment, the at least one adjustable height column comprises two adjustable height columns spaced apart to provide additional space therebetween.

The present disclosure includes disclosure of methods of calculating remaining battery runtime in a mobile battery powered medical cart, comprising determining a set power consumption rate (Pset), wherein Pset is the average power consumption of all electronic devices and accessories connected to the battery powered medical cart, and wherein Pset is determined during production or manufacture of the battery powered mobile medical cart; and applying a custom runtime algorithm, wherein remaining battery runtime is calculated by taking remaining battery capacity (in Watt/hour) and dividing it by the set power consumption rate (Pset). In at least one embodiment, the method further comprises displaying the remaining battery runtime on an illuminated glass overlay positioned on a top surface of the upper workstation area of the mobile battery powered medical cart. In at least one embodiment, the remaining battery runtime is communicated to a user via haptic feedback.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

As such, an overview of the features, functions and/or configurations of the components depicted in the various figures will now be presented. It should be appreciated that not all of the features of the components of the figures are necessarily described and some of these non-discussed features (as well as discussed features) are inherent from the figures themselves. Other non-discussed features may be inherent in component geometry and/or configuration. Furthermore, wherever feasible and convenient, like reference numerals are used in the figures and the description to refer to the same or like parts or steps. The figures are in a simplified form and not to precise scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1:
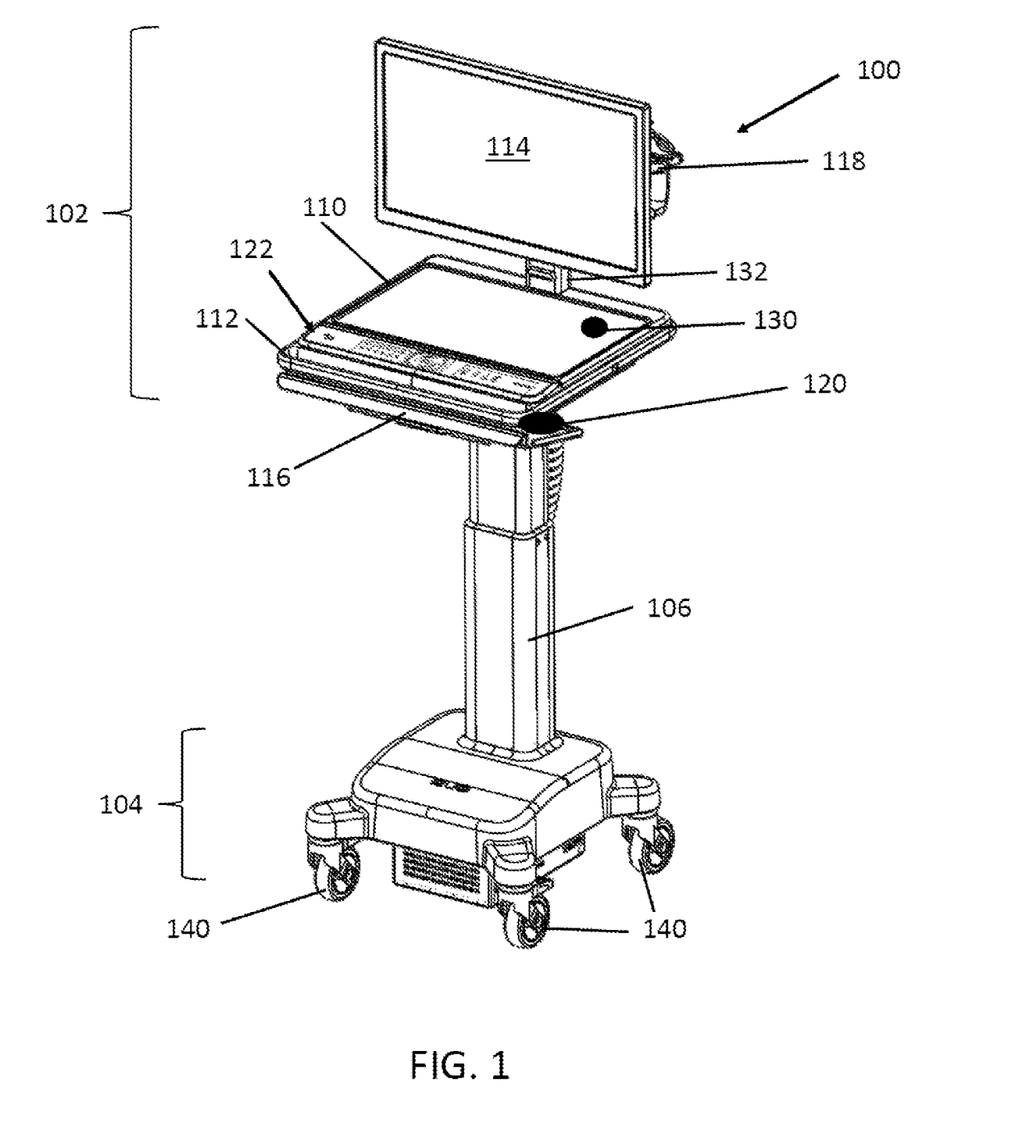
FIG. 1 illustrates a perspective front view of a first embodiment of a mobile battery powered medical cart having an upper workstation area and a lower wheeled base area.

The present disclosure includes various battery powered mobile medical carts 100, systems, and methods for operation of a battery powered mobile medical cart 100. An exemplary battery powered mobile medical cart 100 of the present disclosure may include a standing desk height tower having an upper workstation area 102 and a lower wheeled base area 104, as shown in FIG. 1. These battery powered mobile medical carts 100 can be utilized to improve efficiency in hospitals and other medical or health care settings, as well as in various other operations and industries. These lithium battery (or other battery) powered medical carts 100 are powered by at least one rechargeable lithium battery in the lower base portion 104 to support the electronic components (such as the computer monitor 114, keyboard 116, barcode reader/scanner 118, printer, computer mouse 120, artificial intelligence hub 130, and technology bay 136, including RFID system, GPS, WiFi, Bluetooth, etc.) needed for performing medical related tasks. As will be discussed in more detail below, a sliding battery power bay 202 in the lower wheeled base area 104 may be modular or reconfigurable and sized to receive more than one battery 200 therein to adjust the battery life or runtime of the mobile medical cart 100.

As shown in FIG. 1, the battery powered mobile medical cart 100 may comprise a standing desk height tower/cart having an upper workspace area 102 connected to a lower wheeled base area 104. The upper workspace area 102 and lower wheeled base area 104 can be connected by an elongated adjustable height column 106, such as shown in FIG. 1. The at least one adjustable height column 106 is configured to be vertically adjustable to change the height of the upper workspace area 102 to comfortably accommodate workers having different heights. In some embodiments, mobile medical cart 100 may comprise more than one adjustable height column (as will be described below with reference to FIGS. 5 and 6). The upper workstation area 102 may generally comprise several electronic components, while the lower wheeled base area 104 may generally comprise the battery power bay 202 (described in further detail herein) and wheels 140 to roll or move the entire battery powered mobile medical cart 100 anywhere necessary for performing employee tasks.

Figure 8:
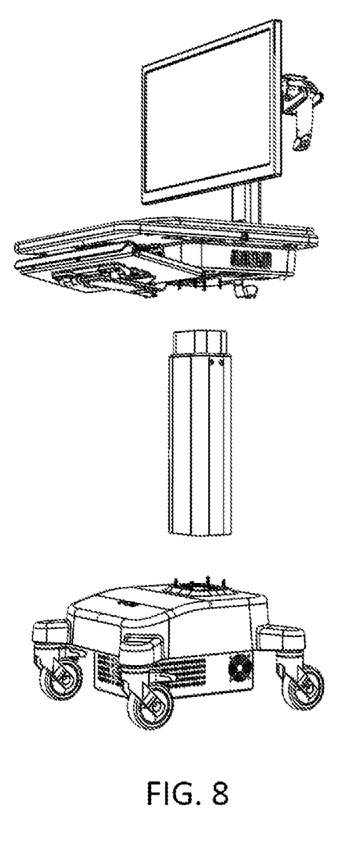
FIG. 8 illustrates a perspective view of the simple assembly of an exemplary mobile battery powered medical cart.
Figure 9:
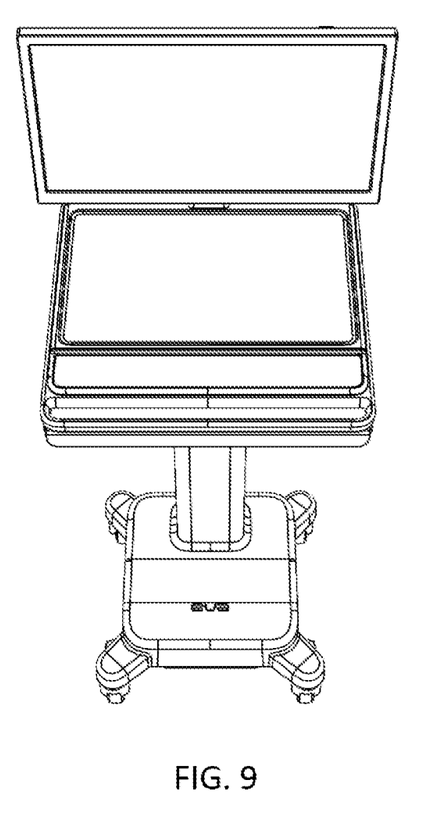
FIG. 9 illustrates a top view of an exemplary mobile battery powered medical cart formed of highgrade aluminum.

As shown in FIG. 1, battery powered mobile medical cart 100 may generally comprise four wheels 140 attached to lower base area 104, which may be formed of a metal and/or rigid plastic frame. The frame may be a highgrade aluminum frame to provide strength and durability, while remaining very lightweight and easy to maneuver (FIG. 9 shows an aluminum frame). The workstation 100 may be assembled simply (such as using only 8 total screws, for example, as shown in FIG. 8) to provide easy assembly and maintenance (reducing downtime) and may further use stainless steel fasteners to provide corrosion resistance. In one embodiments, the lower wheeled base area 104 may be formed of an aluminum die-cast base, for example. While four wheels 140 are shown for purposes of illustration, it should be understood that more than four wheels, or fewer than four wheels, may also be utilized herein. The wheels may be 100 mm precision ball bearing caster wheels with locks, for example. The lower wheeled base area 104 may further comprise a sliding battery power bay 202, shown in FIG. 3 and described in more detail herein below, for receiving a battery 200 therein.

The lower wheeled base area 104 is coupled to upper workstation area 102 by at least one adjustable height column 106, shown in FIG. 1, which may also be formed of a metal or rigid plastic frame. The adjustable height column 106, shown in FIG. 1, may be partially hollow to provide a conduit to electrically couple the electronic components on the upper workstation area 102 with the battery in the lower wheeled base area 104. The adjustable height column 106 may be configured to move vertically up and down electronically so that the overall height of the upper workstation area 102 can be changed to comfortably accommodate workers of different heights. In some embodiments, the at least one adjustable height column may comprise interior ultra high molecular weight (UHMW) low friction tape to provide smooth and stable vertical motion and may be adjustable via controls positioned on glass overlay display 122 (described in more detail herein below). The interior UHMW low friction tape may also account for any gaps due to tolerance stack-up and result in a more sturdy column 106 assembly.

Figure 2:
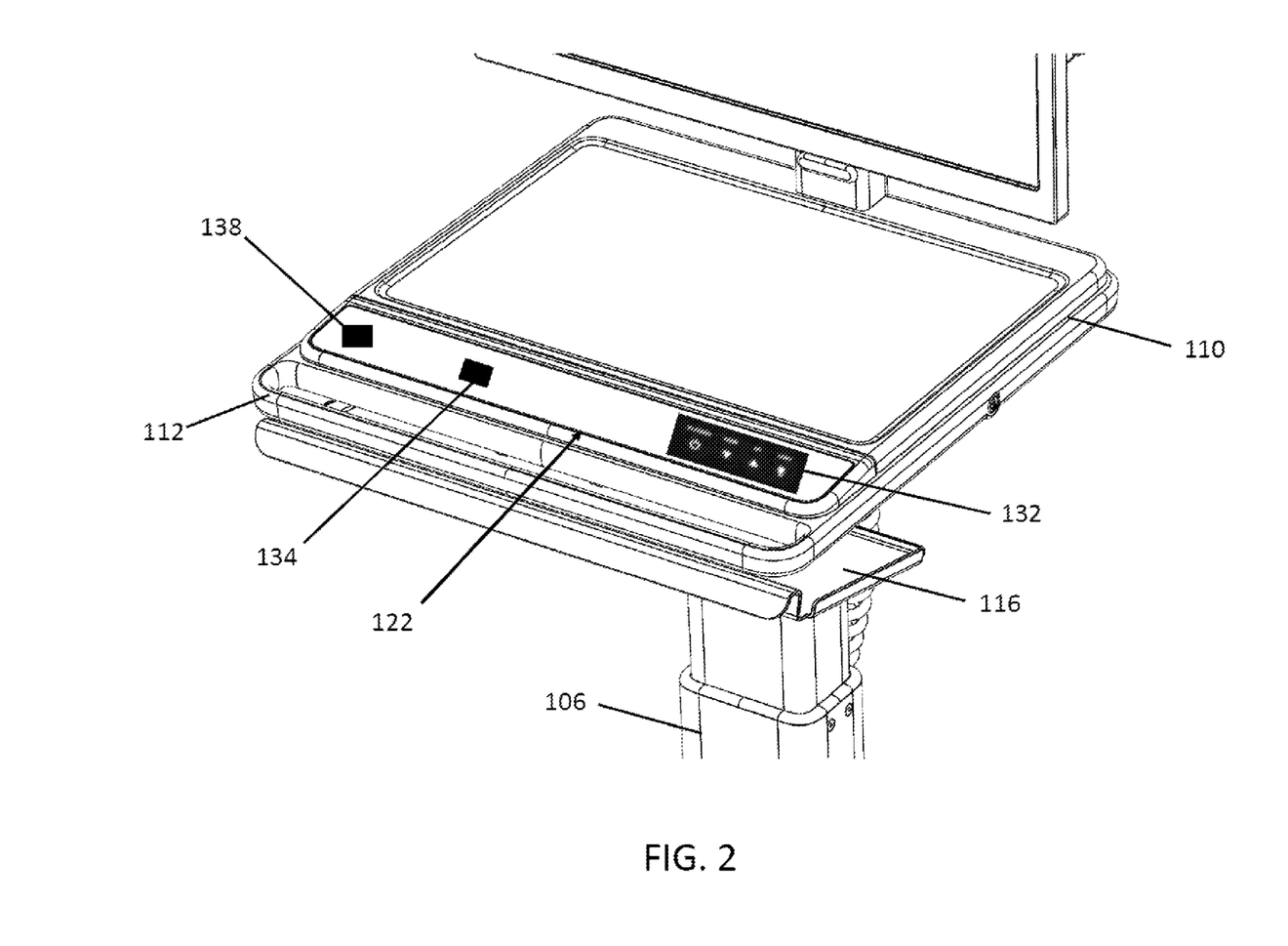
FIG. 2 illustrates an exemplary upper workstation area of a battery powered mobile medical cart of the present invention.

As shown in FIGS. 1 and 2, the upper workstation area 102 may generally comprise a worksurface area 110, such as top cover, having several electronic components thereon and a handle or handle bar 112 attached thereto, all of which are adjustable in height due to the adjustable height column 106. The work surface area 110 may be a removable top cover, so that components below the worksurface 110, such as a technology bay 136 (described in more detail below) can be accessed for component maintenance and/or replacement. The handle bar 112 may run the length or width of the perimeter of the worksurface area 110, so that a user can easily grasp the handle bar 112 to roll and guide the movement of the mobile medical cart 100. In some medical settings, the medical cart 100 may need to be moved frequently and/or long distances thus, handle or handle bar 112 may be a comfortable 1" diameter grip handle bar, for example.

Figure 5:
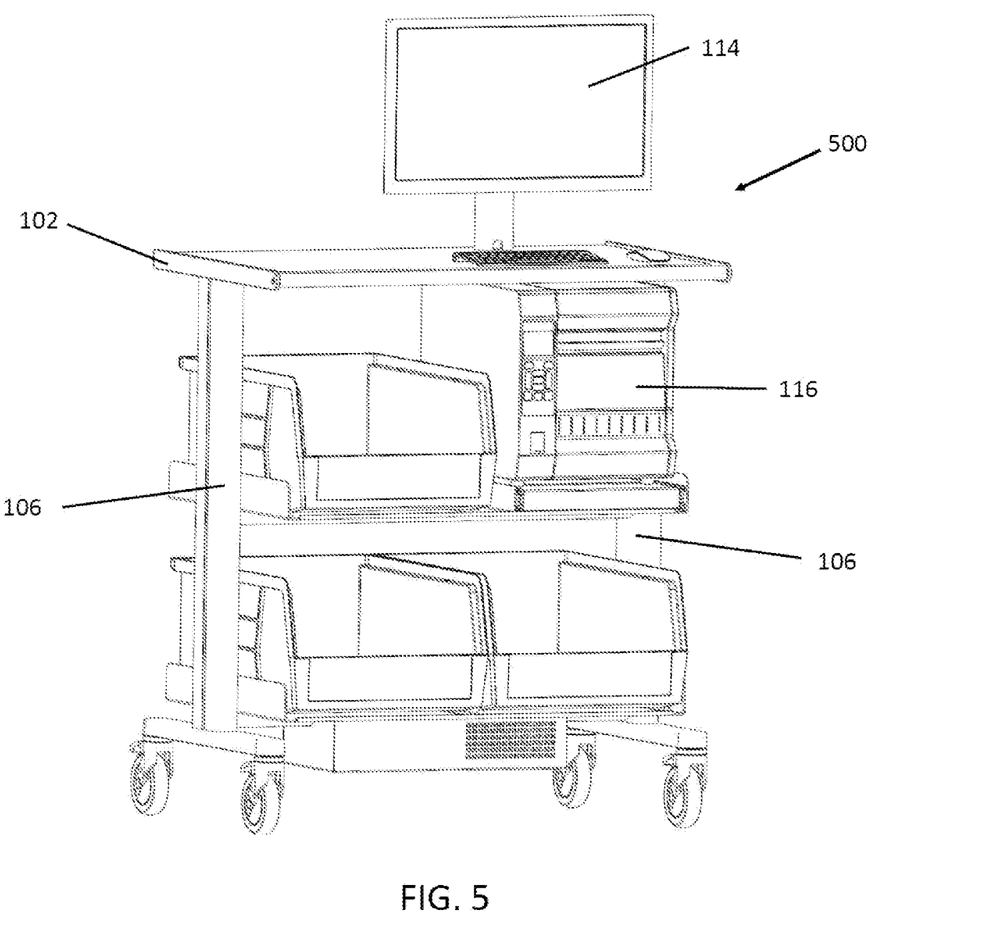
FIG. 5 illustrates a perspective view of an embodiment of a mobile battery powered medical cart having a large upper workstation area as well as a computer, monitor, printer etc.
Figure 6A:
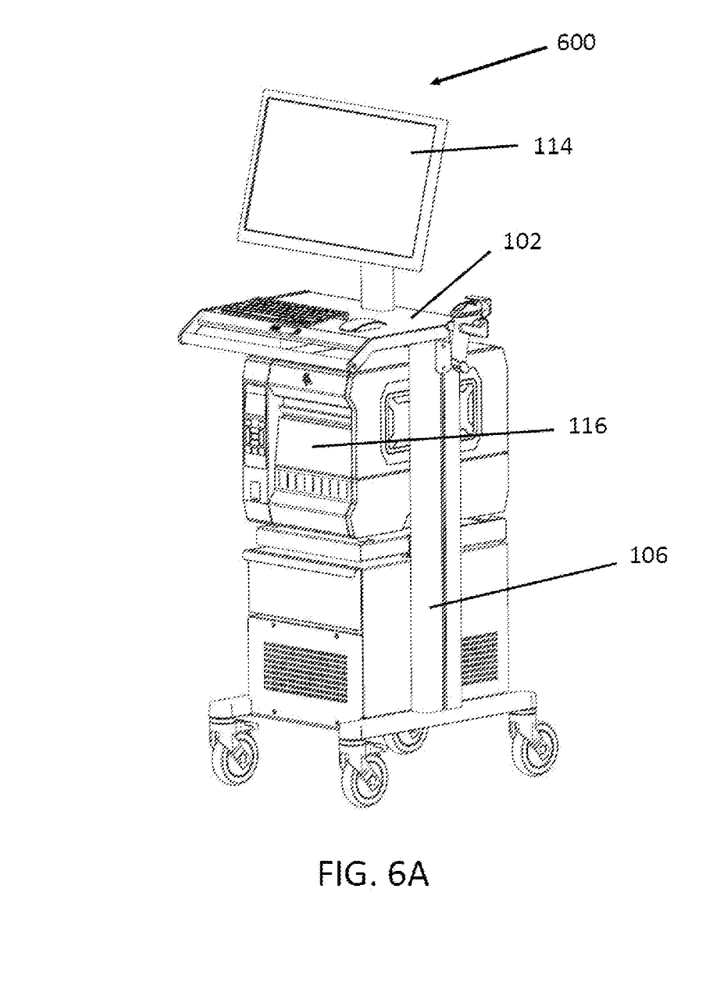
FIGS. 6A and 6B illustrates a perspective view of another embodiment of a mobile battery powered medical cart having a computer, monitor, printer, etc.
Figure 6B:
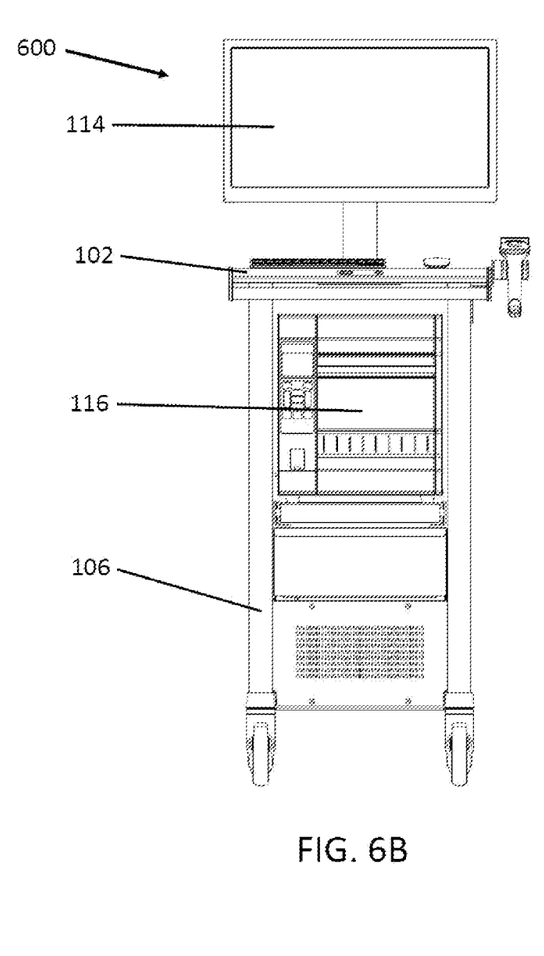

The top worksurface area 110, shown in FIG. 2, may include a mounted computer and/or monitor 114, a slide out keyboard 116, a barcode reader/scanner 118, a mouse 120, and space for a voice-activated smart hub or artificial intelligence hub 130. The computer and/or monitor 114 may comprise a laptop, tablet, or simply a monitor or display screen 114 (with the computer stored below the worksurface area 110, as shown in FIGS. 5 and 6, for example). The computer and/or monitor 114 (or any other type of display or screen) may be mounted to the worksurface area 110, so that it is easily visible by a worker standing in front of the worksurface area 110. The monitor 114 may be coupled to the worksurface area 110 by a bracket or small extrusion 132 with a partially hollow area for wire routing to extend from the monitor 114 to the lower tech bay 136 (described in more detail below). The bracket or small extrusion 132 may further include an integrated LED light for illumination of the worksurface area 110.

The top worksurface area 110 may include space for a voice-activated smart hub 130. The voice-activated smart hub 130 may be an integral part of the computer (located in technology bay 136), or may be a separate component 130, such as an Amazon Echo Dot Google Home®, Vocera®, or a similar voice-activated platform using artificial or machine intelligence (i.e., machine mimicking human cognitive function), mounted to or resting on worksurface area 110. The voice-activated smart hub may interact with the hospital or medical office software database(s) and/or WiFi to send and receive patient and other medical information. The voice-activated smart hub 130 may help medical employees answer questions or use a hands-free device to send and receive information, for example. Equipping a battery powered medical cart 100 with an artificial intelligence hub 130 will assist medical employees in performing their jobs faster and more efficiently and will establish the foundation for future artificial intelligence software within a medical setting.

The upper workstation area 102, shown in FIG. 1, may further include a slide out keyboard tray 116 for holding a keyboard (also referred to herein as 116) and mouse. The slide out keyboard tray 116 may be stored or recessed beneath the top worksurface area 110 or may be pulled out for use. The keyboard 116 may be illuminated by integrated LED lighting on the underside of the top worksurface area 110. The keyboard tray 116 may further comprise a computer mouse 120 or other touch pad control operably coupled to computer (in technology bay 136) and/or monitor 114. The upper workstation area 102 may further include a barcode reader/scanner 118. Barcode reader/scanner 118 (best shown in FIG. 3) and barcode reader/scanner holder 118 (implying an apparatus for retaining a barcode reader/scanner) are used interchangeably herein. Barcode reader/scanner 118 can refer to a holder and/or scanner with or without a holder, can support standard barcode scanner models, and can include components and accessories to charge the same. The upper workstation area 102 may further comprise a lockable drawer or other storage area for storing medical supplies or extra batteries for the cart 100.

Figure 3:
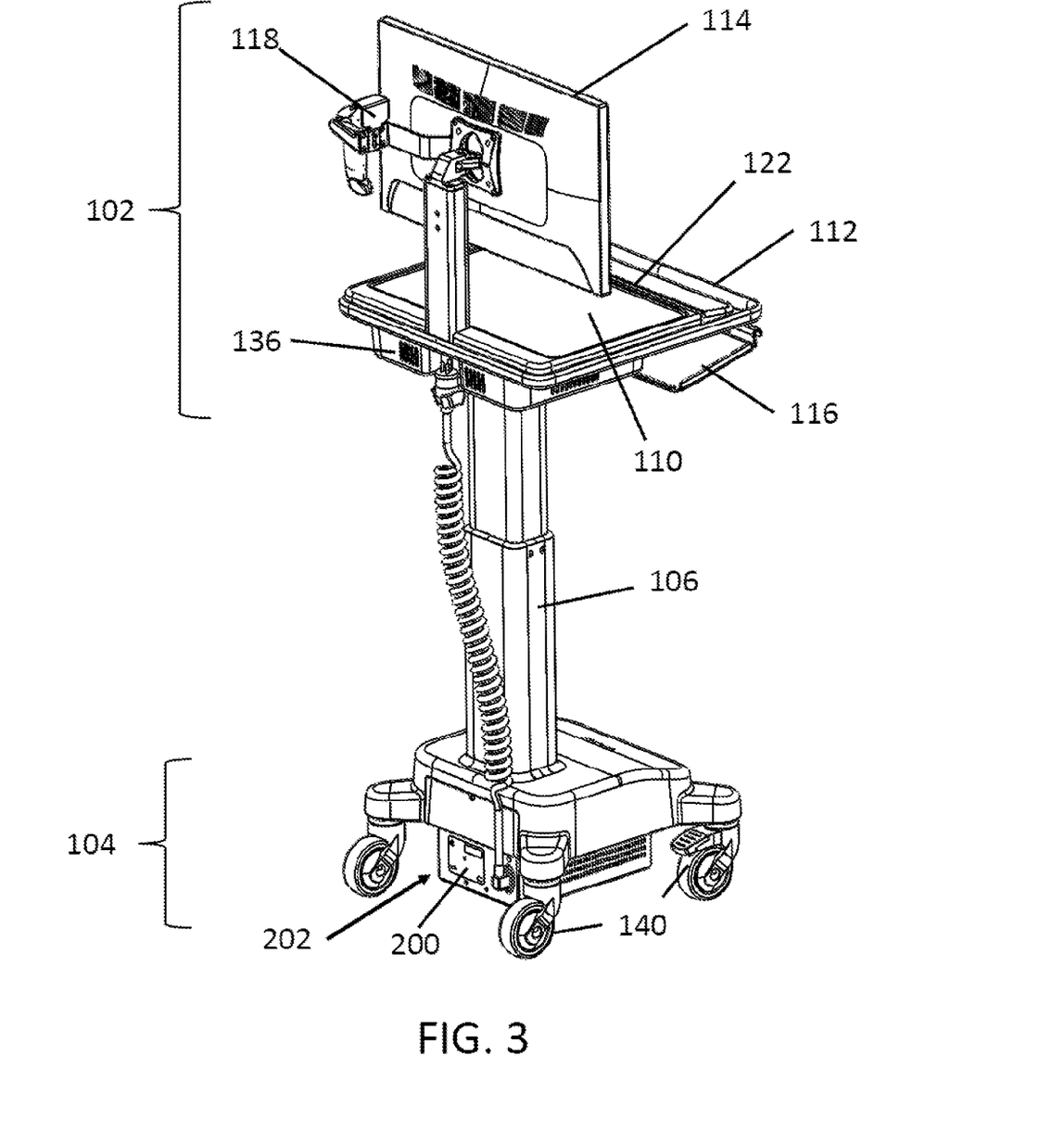
FIG. 3 illustrates a perspective rear view of a first embodiment of a mobile battery powered medical cart showing the pull-out access to the cart power system.
Figure 7A:
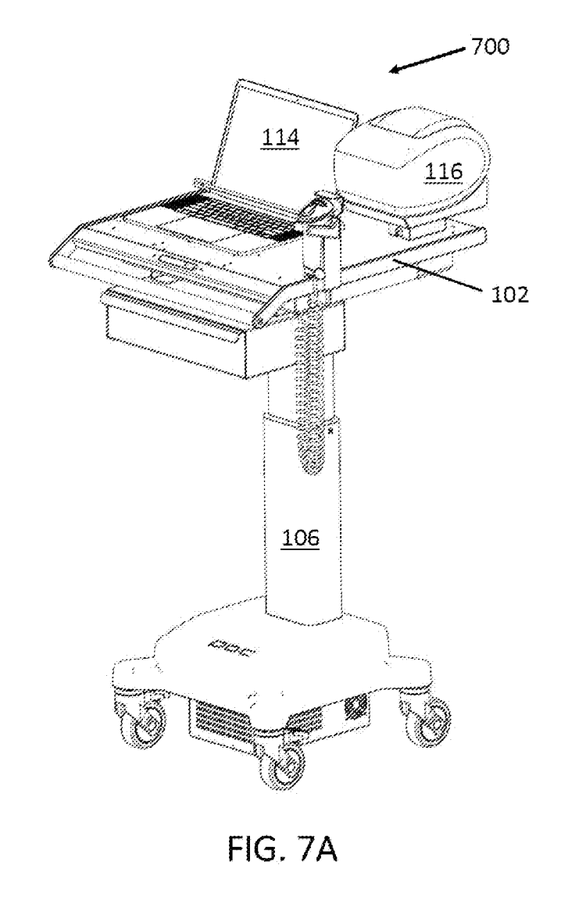
FIGS. 7A and 7B illustrates a perspective view of yet another embodiment of a mobile battery powered medical cart having a laptop computer, etc.
Figure 7B:
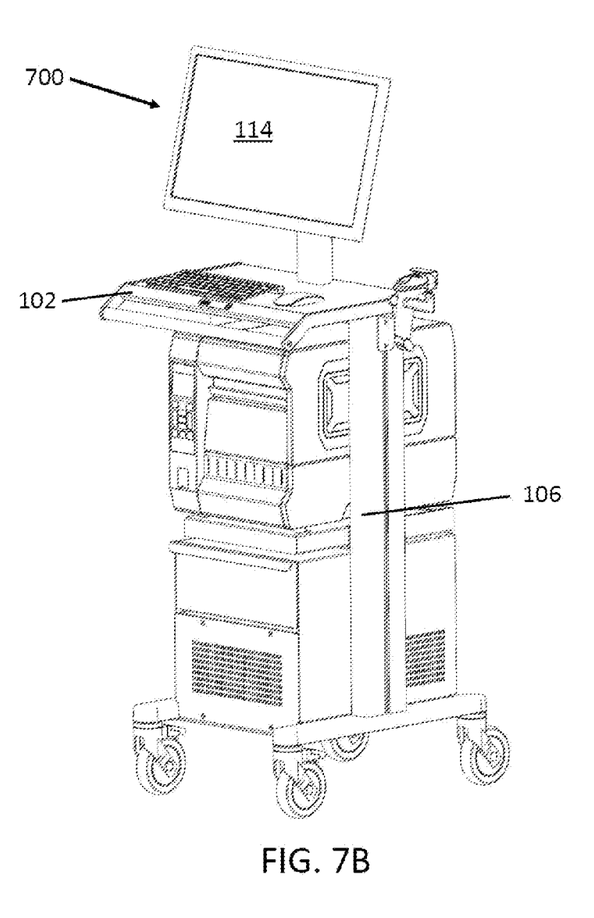

The mobile battery powered medical cart 100 may further comprise a computer (shown generally as 136 in FIG. 3). Computer 136 represents various types of computing devices (e.g. laptop PCs, hard drives, tablets, and phones). Computer 136, as referenced herein, is a general term for a computing device, which may include, but is not limited to, a laptop computer, a tablet, a processor, and the like. Computer 136, monitor 114, keyboard 116, barcode reader/scanner 118, printer, mouse 120, and artificial intelligence hub 130 are shown herein for purposes of illustration, but some embodiments may comprise additional, or fewer, electronic components as being within the scope of the present disclosure. In some embodiments, some or all of the electronic components (i.e., computer 136, monitor 114, keyboard 116, barcode reader/scanner 118, printer, mouse 120, artificial intelligence hub 130, etc.) may be stored below the upper workstation area 102, as best shown in FIGS. 5 and 6. In other embodiments, a smaller medical cart may comprise only a laptop computer and printer positioned on the worksurface area 110, as shown in FIG. 7.

The top worksurface area 110, shown in FIG. 2, may also include a glass overlay display 122. The glass overlay display 122 may generally comprise push or touch button controls with haptic feedback and/or an illuminated display showing relevant mobile medical cart 100 information. For example, the haptic feedback of the glass overlay display 122 may vibrate, or otherwise signal a user, when the cart 100 needs a battery replacement. The glass overlay display 122 may display remaining battery life and/or battery charging status, whether or not the cart 100 is plugged in, whether or not the cart 100 is in use, etc. This remaining battery life may be more precisely calculated by application of a custom runtime algorithm for increased accuracy. The runtime algorithm may take the remaining battery capacity and divide it by a set power consumption (set by the installer or integrator on the utility software at production or manufacture) to obtain a more accurate battery runtime reading.

The glass overlay display 122 may further be formed of a chemical resistant and bacterial resistant material. This bacterial and chemical resistance will be very desirable in any medical setting to prevent the spread of bacteria or other pathogens. This anti-bacterial glass overlay display 122 may be very advantageous, especially on such a frequently touched surface, to protect the users from infection, thus making it more user-friendly surface. The glass overlay display 122 may also be formed of a more durable chemical resistant material, making it easier to clean, thus protecting the user interface and controls 132, 134 thereon from damage when cleaning. In some embodiments, the glass overlay display 122 may also be made out of plastic, or some other transparent material other than glass.

As shown in FIG. 2, the glass overlay display 122 may further include controls 132 for adjustment of the adjustable height column 106 and for controlling lighting on worksurface area 110. The controls 132 for height adjustment of column 106 and lighting of worksurface area 110 and/or keyboard 116 may comprise haptic feedback controls. The glass overlay display 122 may further include controls 134 for passcode inputs used to authenticate user access to the computer (in technology bay 134) or passcodes to open/access a locked drawer on the cart 100. Patient privacy and other medical information is of paramount importance and thus, access to the computer 134 on the mobile battery powered cart 100 must be protected via user authentication and/or passwords and/or an RFID reader 138 for employee identification badges. The RFID reader 138 may also be positioned on the glass overlay display 122 and provides another method of authentication used to ensure access is only granted to employees with the proper identification badge (RFID chip). Mobile battery powered medical carts 100 may be left unattended at times and these security features (i.e., password protection, RFID authentication, etc.) ensure that confidential medical information may not be accessed by another other than authorized medical personnel. These control features 132, 134 of the glass overlay display 122 are advantageous for providing medical employees with additional relevant information about the mobile medical cart 100 to increase overall employee efficiency in medical settings.

As shown in FIG. 3, the top worksurface area 110, may also include a technology bay 136 housing a computer, internal internal radio frequency identification (RFID), global positioning system (GPS), WiFi, and/or Bluetooth Low Energy (BLE) (or Wi-Fi Triangulation, or program similar to iBeacon) systems therein. The RFID may be used for employee identification purposes. The Wi-Fi capability will allow the battery powered medical cart 100 to connect to the hospital's WiFi network. The BLE capability can communicate the cart's location within a medical facility, while the GPS can transmit the cart's location outside of the hospital or medical facility. In very large medical operations, the BLE & GPS can be used simultaneously to monitor the location of many mobile medical carts 100, such as to determine the number of carts in use in on each floor, wing, or section of a hospital medical facility. The Wi-Fi capability will be important for integrating the battery powered medical cart 100 with the existing technology and software. For example, the Wi-Fi may be used to provide important patient information to the medical staff. The Wi-Fi may also help to monitor patient progress and/or may also be used to update the queue for patient priority and other services.

These battery powered medical carts 100 may be used in combination with a tracking and monitoring system to track and monitor an entire fleet of other similar (or identical) medical carts 100. The medical carts 100 using the tracking and monitoring system can all communicate via BLE and/or GPS, such as by using small tracking beacons positioned on the carts themselves 100, as well as all around the hospital or medical facility. This tracking system may also use its own secure network and provide efficiency monitoring and fleet management. For example, if a cart 100 is constantly being plugged in when the battery charge is at 80%, then the cart 100 is not being used efficiently and the tracking and monitoring system can send the administrator a notice to alert them that they could be using the battery life/runtime more efficiently. The tracking and monitoring system can also alert the administrator about the health of the fleet of carts 100, errors detected, and can pinpoint problems or areas needing improvement.

Positioning the upper workstation area 102 at a comfortable and ergonomic height for each employee (via adjustable height column 106) provides easy viewing of the screen or monitor 114, as well as easy access to the keyboard 116, worksurface area 110, computer mouse 120, barcode reader/scanner 118, and artificial intelligence hub 130. In this embodiment, a user/employee can easily view the computer screen or monitor 114 while pushing the battery powered mobile medical cart 100 through the hospital or medical facility. Portable barcode scanners, portable printers, and/or PDAs can also have a docking station on the cart 100 so that the user can dock items to free up their hands while working.

The battery powered medical cart 100 may operate as a mobile base workstation, for holding and powering the electronic components (such as monitor 114, keyboard 116, barcode reader/scanner 118, mouse 120, and artificial intelligence hub 130, computer in technology bay 136, RFID reader 138, etc.) using a battery 200 (or multiple batteries) located in the lower wheeled base area 104. As shown in FIG. 3, the battery powered medical cart 100 comprises at least one battery 200 (which may also be referred to as a power system, such as being AC powered with a cable). The battery 200, or batteries 200, may comprise lithium batteries, which are rechargeable (so to cover a desired amount of time, such as at least one or two work shifts, for example) and/or swappable, and/or removable. While the embodiments described herein utilize a lithium battery, other batteries may also be used herein within the scope of the present invention. Additionally, in some embodiments, a DC battery setup may be utilized to extend battery runtime to greater than 40 hours.

The lithium battery or batteries 200 may be operably coupled to the electronic components (such as monitor 114, keyboard 116, barcode reader/scanner 118, mouse 120, and artificial intelligence hub 130, computer in technology bay 136, RFID reader 138, etc.) to provide power. Additionally, the lithium battery or batteries 200 may be large enough to provide battery power for at least one employee shift, or approximately 8 hours. However, in other embodiments, the lithium battery or batteries 200 will be large enough to provide power for multiple employee shifts. The lithium battery or batteries 200 can be recharged, such as by plugging it in to a wall outlet and/or by replacing the battery 200 with another fully charged battery 200.

In one embodiment, shown in FIG. 3, the at least one battery 200 is housed in a sliding power bay 202 located in the lower base area 104 of the medical cart 100. The battery or batteries 200 may be housed within a sliding battery power bay 202 to provide easy access to a user needing to perform maintenance or change the battery 200. The sliding battery power bay 202 may easily roll or operate to slide open and closed via ball bearing drawer slides, for example.

Figure 4:
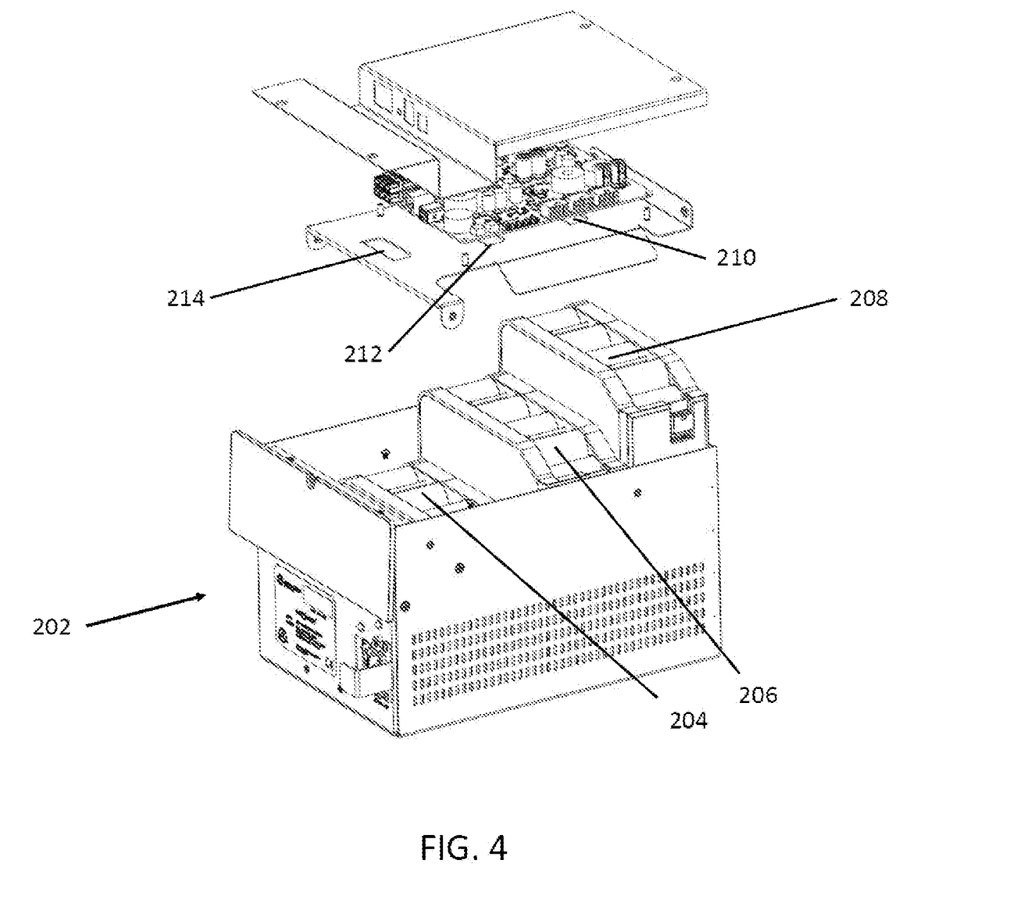
FIG. 4 illustrates an exemplary embodiment of a sliding battery power bay having modular battery compartments.

As shown in FIG. 4, the sliding battery power bay 202 may be modular or reconfigurable to accommodate different numbers of batteries therein. FIG. 4 illustrates an exemplary configuration of a sliding battery power bay 202 having three batteries, 204, 206, and 208 therein. Each battery 204, 206, 208 may have its own compartment or pocket within the sliding battery power bay 202. The batteries 204, 206, 208 and/or battery compartments may be separated by battery separating tabs 210, 212, 214, to help reduce heat and improve performance of the individual batteries. In this embodiment, the sliding battery power bay 202 is configurated to hold three batteries 204, 206, and 208, thus giving the medical cart triple the runtime of a cart with only one battery.

This reconfigurable or modular design of the sliding battery power bay 202 allows the runtime of the medical cart to be adjusted by providing a different number of batteries in the sliding battery power bay 202, thus allowing the runtime and overall cost of the medical cart to be adjusted to meet consumer needs and budgets. For example, a sliding battery power bay 202 having a single battery 200 will have a shorter runtime and a lower cost. However, a sliding battery power bay 202 having multiple batteries (such as 204, 206, 208) will have a longer runtime and a higher cost. The size of the compartments and/or the sliding battery power bay 202 can be changed as desired to correspond to the desired number of batteries or runtime or number of hours in an employee shift. For example, the medical cart having a single battery 200 may be a 'single shift' medical cart, while the medical cart having multiple batteries 200 may be a 'multiple shift' medical cart. In one example, a single battery may have a runtime of approximately 13 hours, a dual battery may have a runtime of approximately 26 hours, and a triple battery may have a runtime of approximately 40 hours. However, the sliding battery power bay 202 may be configured to accommodate any number of batteries and/or compartments therein, having various runtimes, as will be understood by those of ordinary skill in the art.

In one embodiment, extra or spare batteries may be stored elsewhere on the cart 100, such as in a bracket (not shown) on the adjustable height column 106, or in a locked storage drawer (not shown). Storing additional batteries on the mobile medical cart 100 itself will allow employees to easily and quickly swap or replace batteries during a work shift to maximize efficiency. Employees can simply pull open the sliding battery power bay 202, remove an extra battery, swap the old dead battery for the new extra (fully charged) battery, push the sliding battery power bay 202 closed, and resume work operations.

FIG. 5 illustrates a perspective view of an embodiment of a mobile battery powered medical cart 500 having a larger upper workstation area 102 with a monitor 114, as well as a full computer and printer 116, etc. positioned below the upper workstation area 102. In this embodiment, it should be noted that monitor 114 may be replaced with a laptop or tablet computer. Further, the medical cart 500 may comprise two (i.e., dual) adjustable height columns 106 for additional support. This embodiment provides additional storage space (shown as bins in FIG. 5) between the two adjustable height columns 106 for conveniently storing more order fulfillment supplies (i.e., labels, stickers, envelopes, boxes, tape, and other related packing and shipping materials), while still providing mobility and the full computing abilities necessary for employees to efficiently perform order fulfillment tasks.

FIGS. 6A and 6B illustrate a perspective view of another embodiment of a mobile battery powered medical cart 600 having a smaller upper workstation area 102 and monitor 114, while still providing the full computer and printer 116, etc. necessary for employees to efficiently perform order fulfillment tasks. In this embodiment, the medical cart 600 may also comprise two (i.e., dual) adjustable height columns 106 for additional support. This medical cart 600 may have a smaller profile than the medical cart 500 shown in FIG. 5, for increased maneuverability within an order fulfillment setting, while still providing the full computing capabilities for efficient order fulfillment operations, thus permitting more medical carts 600 (i.e., more employees) to be positioned and working within a small space.

FIGS. 7A and 7B illustrate a perspective view of yet another embodiment of a mobile battery powered medical cart 700 having a laptop computer 114 positioned on the upper workstation area 102. This embodiment provides the flexibility of a removable laptop computer 114 for order fulfillment employees, while still providing a smaller profile medical cart 700 having some storage and printing capabilities necessary for order fulfillment operations within smaller spaces.

While various embodiments of devices and systems and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A mobile battery powered medical cart, comprising:
a wheeled base portion having a battery power bay for service and battery replacement therein;
an upper workstation area having a monitor and a glass overlay display, wherein the glass overlay display is positioned on a top surface of the upper workstation area and has anti-bacterial and chemical resistant properties and comprises haptic feedback controls;
at least one adjustable height column operably coupling the wheeled base portion and the upper workstation area and electronically coupling the battery in the wheeled base portion with the monitor and haptic feedback controls in the upper workstation area; and
wherein the haptic feedback controls vibrate to signal a user when the cart needs a battery replacement.

2. The mobile battery powered medical cart of claim 1, wherein the haptic feedback controls are used to control passcode input, adjustment of the adjustable height column, workspace illumination controls, and display of remaining battery runtime via a custom runtime algorithm.

3. The mobile battery powered medical cart of claim 1, wherein remaining battery runtime is calculated by taking remaining battery capacity (in Watt/hour) and dividing it by the set power consumption rate (Pset), wherein Pset is the average power consumption of all electronic devices and accessories connected to the battery powered mobile medical cart, and wherein Pset is determined during production or manufacture of the battery powered mobile medical cart.

4. The mobile battery powered medical cart of claim 1, further comprising a voice activated smart hub or artificial intelligence hub.

5. The mobile battery powered medical cart of claim 1, further comprising a technology bay in the upper workstation area to house a computer, an RFID reader, Wi-Fi, BLE, and/or GPS systems.

6. The mobile battery powered medical cart of claim 1, further comprising an RFID device that is integrated with the glass overlay display.

7. The mobile battery powered medical cart of claim 1, wherein the monitor further comprises a laptop computer or tablet.

8. The mobile battery powered medical cart of claim 1, further comprising a computer.

9. The mobile battery powered medical cart of claim 1, wherein the at least one adjustable height column comprises two adjustable height columns spaced apart to provide additional space therebetween.

10. A mobile battery powered medical cart, comprising:
a wheeled base portion having a battery power bay for receiving at least one swappable battery therein;
an upper workstation area having electronic components operably coupled to, and powered by, the at least one swappable battery in the power bay;
a glass overlay display positioned on a top surface of the upper workstation area and having anti-bacterial and chemical resistant properties, and providing a display for remaining battery runtime calculated via a custom runtime algorithm;
a spare battery stored on the adjustable height column, wherein the spare battery is connected to the electronic components when placed in the battery power bay; and
a technology bay to house integrated RFID, Wi-Fi, BLE, and/or GPS systems.

11. The mobile battery powered medical cart of claim 10, wherein the battery power bay comprises modular compartments for receiving multiple batteries therein, wherein more than one battery may be used to adjust runtime of the cart.

12. The mobile battery powered medical cart of claim 11, further comprising battery separating tabs disposed between the battery compartments of the battery power bay to reduce heat and/or improve individual battery performance.

13. The mobile battery powered medical cart of claim 10, wherein the glass overlay display further comprises haptic feedback controls for passcode input, adjustment of at least one adjustable height column, workspace illumination controls, and display of remaining battery life via custom runtime algorithm.

14. The mobile battery powered medical cart of claim 10, wherein remaining battery runtime is calculated using an algorithm, taking remaining battery capacity (in Watt/hour) and dividing it by the set power consumption rate (Pset), wherein Pset is the average power consumption of all electronic devices and accessories connected to the mobile battery powered medical cart, and wherein Pset is determined during production or manufacture of the mobile battery powered medical cart.

15. The mobile battery powered medical cart of claim 10, further comprising a monitor.

16. The mobile battery powered medical cart of claim 10, further comprising a computer.

17. The mobile battery powered medical cart of claim 16, wherein the computer is positioned below the upper workstation area.

18. A method of calculating remaining battery runtime in a mobile battery powered medical cart, comprising:
- determining a set power consumption rate (Pset), wherein Pset is the average power consumption of all electronic devices and accessories connected to the battery powered medical cart, and wherein Pset is determined during production or manufacture of the battery powered mobile medical cart; and
- applying a custom runtime algorithm, wherein remaining battery runtime is calculated by taking remaining battery capacity (in Watt/hour) and dividing it by the set power consumption rate (Pset);
- vibrating a haptic feedback control on the mobile battery powered medical cart to signal the remaining runtime is low and a battery replacement is needed.

19. The method of claim 18, further comprising displaying the remaining battery runtime on an illuminated glass overlay positioned on a top surface of the upper workstation area of the mobile battery powered medical cart.

20. The method of claim 18, wherein the remaining battery runtime is communicated to a user via haptic feedback.

* * * * *